(12) United States Patent  
Schulman

(10) Patent No.: US 7,136,704 B2  
(45) Date of Patent: Nov. 14, 2006

(54) BLOOD OXYGEN MONITORING SYSTEM AND A LEAD THEREFOR

(75) Inventor: Joseph H. Schulman, Santa Clarita, CA (US)

(73) Assignee: Alfred E. Mann Foundation for Scientific Research, Santa Clara, CA (US)

( * ) Notice: Subject to any disclaimer, the term of this patent is extended or adjusted under 35 U.S.C. 154(b) by 560 days.

(21) Appl. No.: 10/418,860

(22) Filed: Apr. 16, 2003

(65) Prior Publication Data

US 2004/0210263 A1    Oct. 21, 2004

(51) Int. Cl.  
*A61N 1/365* (2006.01)

(52) U.S. Cl. .......................................... 607/22; 600/309

(58) Field of Classification Search ................. 607/22; 600/309  
See application file for complete search history.

(56) References Cited

U.S. PATENT DOCUMENTS

| | | |
|---|---|---|
| 2,913,386 A | 11/1959 | Clark |
| 3,358,690 A | 12/1967 | Cohen |
| 4,202,339 A | 5/1980 | Wirtzfeld et al. |
| 4,399,820 A | 8/1983 | Wirtzfeld et al. |
| 4,428,378 A | 1/1984 | Anderson et al. |
| 4,436,092 A | 3/1984 | Cook et al. |
| 4,467,807 A | 8/1984 | Bornzin |
| 4,566,456 A | 1/1986 | Koning et al. |
| 4,600,017 A | 7/1986 | Schroeppel |
| 4,712,555 A | 12/1987 | Thornander et al. |
| 4,815,469 A | 3/1989 | Cohen et al. |
| 5,007,424 A | 4/1991 | Ahsbahs |
| 5,040,538 A | 8/1991 | Mortazavi |

(Continued)

OTHER PUBLICATIONS

Severinghaus, A Combined Transcutaneous PO2-PCO2 Electrode With Electrochemical HCO3 Stabilization, A Combined Transcutaneous PO2-PCO2 Electrode With Electrochemical HCO3 Stabilization, 1981, pp. 1027-1032, vol. 51, No. 4, Publisher: Journal of Applied Physiology, Published in: San Francisco.

*Primary Examiner*—Robert Pezzuto  
*Assistant Examiner*—Shevon Johnson  
(74) *Attorney, Agent, or Firm*—Malcolm J. Romano

(57) ABSTRACT

An oxygen monitoring system measures the oxygen concentration in a patient's blood for use as a physiological control parameter in rate responsive pacing. The oxygen monitoring system includes an oxygen monitoring circuit embedded in a cardiac stimulation lead and monitors the blood oxygen in a patient's venous system that passes through and into the lead. The oxygen monitoring circuit includes a working electrode, a counter electrode, a reference electrode and an IC chip electrically interconnected between the electrodes and programmed to carry out an oxygen concentration measuring process. Oxygen surrounding the electrodes causes current to flow between the electrodes and the IC chip varies the value of current generated by a current source coupled between the working electrode and counter electrode in a manner to maintain the voltage between the working electrode and reference electrode at a preselected value. The variation of the current source value is a direct measure of the blood oxygen concentration. The oxygen monitoring circuit may comprise an IC chip mounted on one side of a substrate and on the reverse side of which are mounted the electrodes or an IC chip(s) upon which the electrodes are directly mounted. Furthermore, the IC chip, with appropriate insulation may be used in place of the substrate. At least two insulated IC chips may be used, for example in a back to back arrangement, for increased overall sensitivity or redundancy.

34 Claims, 7 Drawing Sheets

U.S. PATENT DOCUMENTS

| | | |
|---|---|---|
| 5,094,876 A | 3/1992 | Goldberg |
| 5,198,771 A | 3/1993 | Fidler |
| 5,298,146 A | 3/1994 | Braden |
| 5,342,406 A | 8/1994 | Thompson |
| 5,411,532 A | 5/1995 | Mortazavi |
| 5,438,987 A | 8/1995 | Thacker et al. |
| 5,497,772 A | 3/1996 | Schulman et al. |
| 5,660,163 A * | 8/1997 | Schulman et al. .......... 600/345 |
| 5,917,346 A | 6/1999 | Gord |
| 5,985,129 A | 11/1999 | Gough |
| 6,088,608 A * | 7/2000 | Schulman et al. .......... 600/345 |
| 6,259,937 B1 * | 7/2001 | Schulman et al. .......... 600/345 |
| 6,351,672 B1 | 2/2002 | Park et al. |
| 6,915,147 B1 * | 7/2005 | Lebel et al. ................. 600/322 |

* cited by examiner

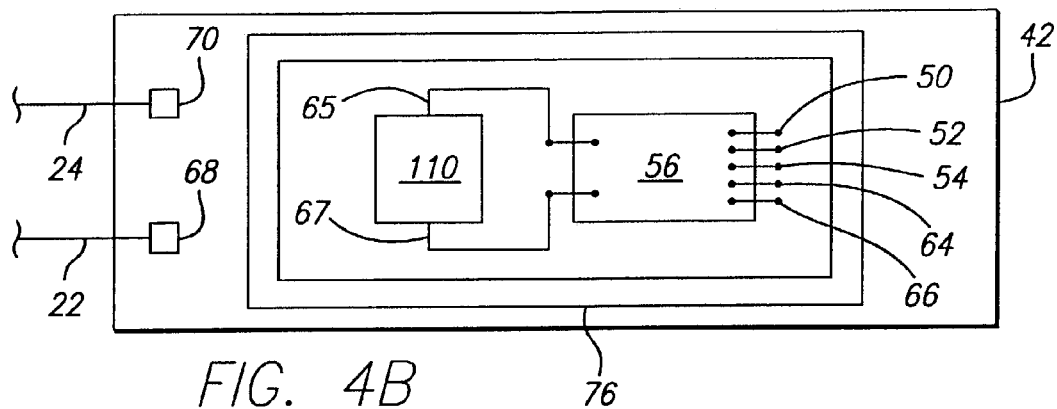
FIG. 4B
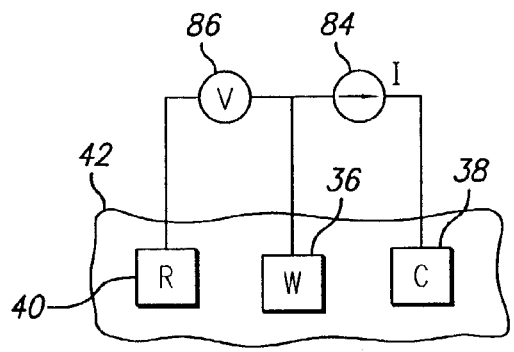
FIG. 5A
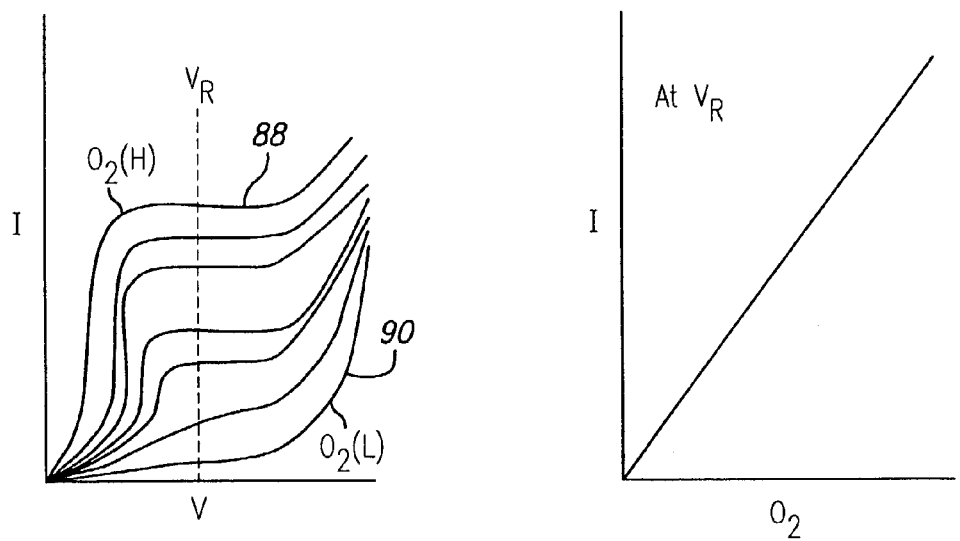
FIG. 5B
FIG. 5C

US 7,136,704 B2

BLOOD OXYGEN MONITORING SYSTEM AND A LEAD THEREFOR

BACKGROUND OF THE INVENTION

1. Field of the Invention

The present invention is directed to a system and lead for monitoring blood oxygen concentration in a patient's venous system.

2. Background

Blood oxygen concentration is a direct indicator of the physiological status and need of a patient. Other indicators include various cardiac timing signals, blood temperature, respiratory rate and blood pressure measured within the chambers of the heart, blood oxygen saturation, as well as physical rate and acceleration. Physiologically responsive pacemakers and cardioverter/defibrillators, both referred to as cardiac stimulation devices, utilize one or more of such indicators as a control parameter(s) to vary cardiac rate in the process of optimizing a patient's cardiac performance to achieve the correct metabolic rate for providing a high level of patient well being. As is recognized in the art, cardiac stimulation devices provide patients having a chronically malfunctioning heart, with selective cardiac therapy in the form typically, of cardiac stimulation pulses in order to maintain proper metabolic rate. Unlike a healthy heart, a malfunctioning heart normally does not adequately respond to physical activity, exercise, stress or emotion, posture changes and sleep conditions. Normal cardiac reaction to physiological need manifests in adjustment of cardiac stroke volume and heart rate with the natural adjustment of such parameters being responsive to immediate need.

To remedy the deficiencies of a malfunctioning heart, cardiac stimulation devices have been widely used to control heart rate and thus metabolic rate. Early devices were not rate responsive and provided a pacing regimen that stimulated the heart at a constant rate under all conditions. The drawback of such devices was that under many conditions they did not provide the proper metabolic rate for patient need. For example, under sleep conditions where the required heart rate is low due to minimal physiological need, the device would pace the heart at too high a rate than required. On the other hand, a constant pacing rate did not adequately respond to a patient's metabolic need under high exercise and stress conditions.

Upon the introduction of rate responsive stimulation devices, a more rapid response to satisfying a patient's physiological need was made available. The intent of such devices was to adjust the patient's cardiac rate on a continual basis for a wide variety of exercise and stress conditions encountered by a patient. A very straightforward technique for controlling cardiac pacing in rate adaptive dual chamber devices is by the use of atrial tracking pacing, especially when the patient has partial or complete AV block. This technique however lacks effectiveness when the patient suffers from atrial fibrillation or sinus bradycardia.

To address this situation, other techniques utilizing the aforementioned indicators of physiological need have been proposed. For example, the use of venous blood temperature has been described by Cook et al., in U.S. Pat. No. 4,436,092. The shortcomings of this device are, lack of rapid response, coarseness of measurement and susceptibility to non-physiological influences such as the ingestion of cold liquids and fever. A second approach is the use of blood pressure at different locations in the heart. One such device utilizing the blood pressure in the atrium, was described by Cohen in U.S. Pat. No. 3,358,690. However, patients with sinus bradycardia and atrial fibrillation are not amenable to this approach. Other devices utilizing blood pressure have been described by Koning et al. in U.S. Pat. No. 4,566,456 and by Scroeppel in U.S. Pat. No. 4,600,017. These devices however, fall short if the patient suffers from sinus bradycardia or atrial fibrillation. Activity sensing, rate responsive devices as described for example by Anderson et al., in U.S. Pat. No. 4,428,378 and by Thornander et al., in U.S. Pat. No. 4,712,555 provide fast response times and good reliability but often are affected by non activity events. For example, if the patient is riding in a vehicle over a bumpy road, the resulting body movement will be erroneously interpreted as physical activity inducing unnecessary pacing rate increases.

Still, another class of devices utilizes blood chemistry as physiologic indicators. The use of blood oxygen saturation has been described by Wirtzfeld et al. in U.S. Pat. Nos. 4,202,339 and 4,399,820; by Bornzin in U.S. Pat. No. 4,467,807; by Cohen in U.S. Pat. No. 4,815,469; by Thompson in U.S. Pat. No., 5,342,406; by Thacker in U.S. Pat. No. 5,438,987; and by Mortazavi in U.S. Pat. Nos. 5,040,538 and 5,411,532. The devices taught by Mortazavi include a light-emitting diode (LED) positioned within a chamber of the heart and arranged such that light emitted from the LED is directed at the blood which then reflects the light to an adjacent light detecting sensor in the form of a phototransistor. Upon delivery of a sensing pulse, the LED commences to emit light and the reflected light is produced in an intensity proportional to the oxygen concentration. Circuitry associated with the phototransistor integrates the voltage proportional to the light's intensity and when the integrated voltage reaches a "prescribed value", current is then shunted away from the LED and the integration process is terminated. The time interval from delivery of the sensing pulse to reaching the "prescribed value" is a measure of the degree of oxygen saturation in the blood. The blood cells change from a blue to a red hue when the myoglobin in the blood cells is saturated with oxygen. This sensing method does not indicate accurately the percentage of oxygen in the blood below the saturation point of the myoglobin. The oxygen sensor circuit includes a diode in series circuit arrangement with a stimulation lead conductor. Pacing pulses are generated having a first polarity, while oxygen sensing pulses are generated having a second polarity opposite to that of the first polarity. Accordingly, this type of arrangement requires a polarity distinction between pacing and sensing pulses. Furthermore, the placement of the sensor is taught to be in the atrium and there is a potential that oxygen monitoring may be compromised if the sensor is located immediately adjacent to or in contact with the atrium wall because there may be an insufficient amount of blood in the area surrounding the sensor to obtain a reliable measure of oxygen concentration.

SUMMARY OF THE INVENTION

Briefly and in general terms, the present invention is directed to a blood oxygen monitoring system that is accurate through the entire oxygen concentration range, and a lead therefor. The system monitors blood oxygen concentration upon the delivery of an oxygen sensing command signal, in the form of a biphasic pulse train, to an oxygen sensor imbedded within a cardiac stimulation lead that is implanted in a patient's venous system. The sensor may also be oriented in the stimulation lead such that it is located in a selected chamber of the heart. The oxygen concentration so determined, may be used as a physiological parameter for controlling the pacing rate of an implanted cardiac stimulation device so as to maintain a patient's proper metabolic rate. The oxygen monitoring circuit is in parallel circuit arrangement with the conductor(s) of a cardiac stimulation lead thereby avoiding the necessity of dedicated polarities for pacing pulses and oxygen monitoring related pulses. Moreover the duration of the oxygen monitoring related pulses are such that they do not induce cardiac muscle contractions akin to those involved in cardiac pacing.

More specifically, the system of the present invention is microprocessor controlled and includes a cardiac stimulation lead which is in direct contact with a patient's venous blood system. The cardiac stimulation lead includes at least one electrical conductor and the oxygen monitoring circuit measures the blood oxygen concentration in the venous blood system. An oxygen monitoring pulse generator is coupled to the microprocessor and is configured to generate a biphasic pulse train containing a preselected number of bits comprising at least address bits, control data bits, parameter information bits and stop bits. The pulse train from the oxygen monitoring pulse generator is received by the oxygen monitoring circuit to commence oxygen monitoring. The oxygen monitoring circuit includes an integrated circuit (IC) chip that is hermetically sealed from blood contact and is programmed to undertake the oxygen concentration monitoring functions. The IC chip is powered by an on board energy storage component that may be recharged from either or both the cardiac stimulation pulses and the oxygen monitoring related pulses.

The oxygen monitoring circuit is fabricated on a substrate and includes a working electrode, a counter electrode and a reference electrode. The electrodes are encased in a gel like oxygen and electrically conductive material. The entire monitoring circuit, as previously mentioned, is imbedded in a cardiac stimulation lead. The lead has an outer sleeve that is transparent to oxygen and that extends the length of the lead. Oxygen passes through the sleeve as well as the gel like material and eventually reaches the electrodes. The IC chip is in electrical communication with the electrodes and includes a current source connected between the working electrode and the counter electrode. The IC chip also monitors the voltage between the reference and working electrodes and adjusts the current source in order to keep the voltage between the reference and working electrodes constant at a specific value. The voltage value selected is that value that causes a current to flow that is directly related to the oxygen concentration level. Upon receipt of an oxygen monitoring start signal, the voltage across the reference electrode and working electrode is examined. If the value is other than a required voltage, the IC chip proceeds to change the value of the current generated by the current source until the voltage across the reference electrode and working electrode, returns to the reference value. The value of the current so required, is a measure of the instantaneous blood oxygen concentration level. This value is communicated back to the microprocessor for processing via an information pulse train generated by the IC chip and transmitted back to the microprocessor along the stimulation lead conductor. The information from the IC chip may be in the form of a monophasic pulse train recognizable by the microprocessor. The times at which the oxygen monitoring related pulse trains are transmitted may be during the time interval between the occurrence of a cardiac T-wave and atrial stimulation pulse. From practice, the invention is characterized in that it provides a very accurate, high reliability and relatively low volume physically small oxygen monitoring apparatus and method.

The oxygen monitoring circuit may be used with a variety of cardiac stimulation leads including bipolar, unipolar and defibrillation leads. In one embodiment, the lead may be connected between the two conductors of a bipolar lead or between the one conductor of a unipolar lead and the "can" which houses the cardiac stimulation device.

BRIEF DESCRIPTION OF THE DRAWINGS

FIG. 4B is a simplified block diagram of the IC chip and an energy storage device mounted on the underside of the oxygen monitoring circuit;

FIG. 5A is an electrical circuit diagram of the electrode interconnection of the oxygen monitoring circuit;

FIG. 5B is, a graph that depicts the relationship between electrical current delivered to the electrodes of the oxygen monitoring circuit and the voltage between the electrodes as a function of oxygen concentration;

FIG. 5C is a graph that depicts the relationship between the electrical current delivered to the electrodes as a function of oxygen concentration at a fixed reference voltage;

DETAILED DESCRIPTION OF THE INVENTION

The following description relates to the best mode presently contemplated for carrying out the invention. This description is not to be taken in the limiting sense, but rather is made merely for the purpose of describing the general principles of the invention. The scope of the invention should be determined with reference to the claims and equivalents thereof.

Figure 1:
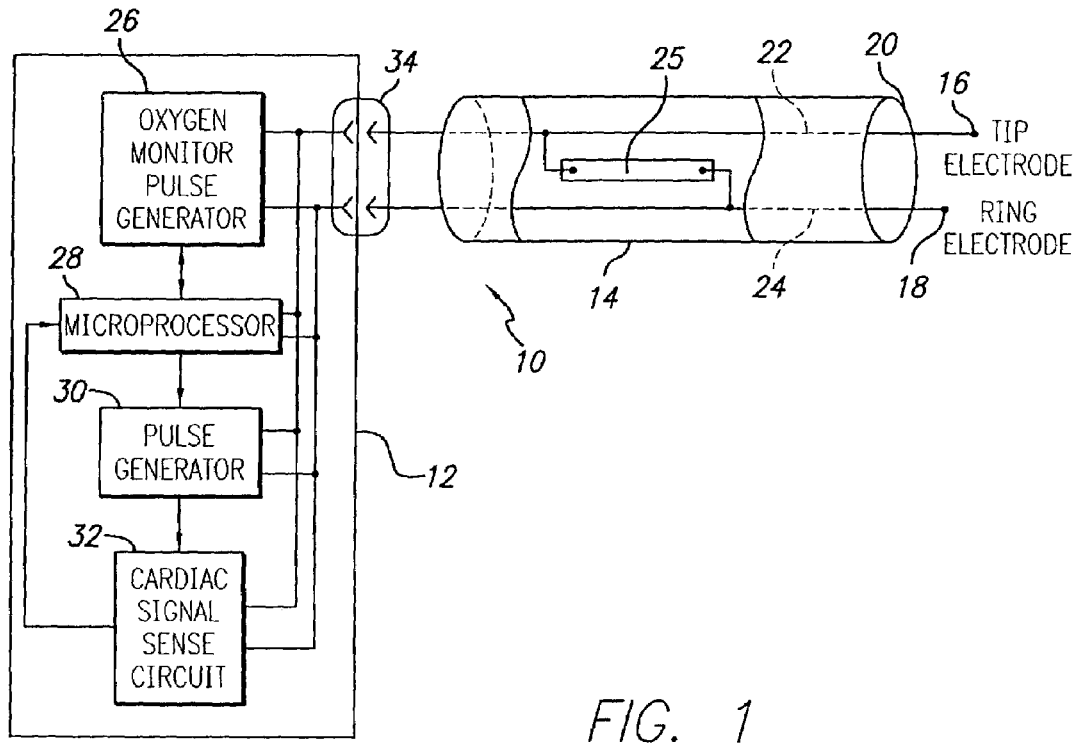
FIG. 1 is a simplified block diagram of a first embodiment in accordance with the present invention including a cardiac stimulation device, and an oxygen monitoring circuit electrically coupled to a bipolar lead.

Referring to FIG. 1, there is shown in block diagram format, an oxygen monitoring system in accordance with the principles of the present invention. The system 10 includes a cardiac stimulation device 12, a cardiac stimulation lead 14 having a tip electrode 16 and a ring electrode 18. Although stimulation lead 14 is shown as being a bipolar lead, as will be discussed later, other lead configurations such as for example unipolar leads are contemplated by this invention. The stimulation lead 14 is of a typical design known in the art having a silicone outer casing 20 and electrical conductors 22 and 24 that are coupled to tip electrode 16 and ring electrode 18 respectively. The electrodes are adapted to be secured to selected cardiac tissue, such as heart muscle, intended for receipt of stimulation pulses. Mounted within the interior of stimulation lead 14 is oxygen monitoring circuit 25 that is electrically coupled across conductors 22 and 24. The cardiac stimulation device 12 includes an oxygen monitor pulse generator 26, a microprocessor 28, a stimulation pulse generator 30 and a cardiac signal sense circuit 32. The stimulation lead 14 is electrically coupled to the stimulation device 12 by means of connector 34. The type of connector 34 will depend upon the type of stimulation lead used and a single lead connector may be used, for example, when a unipolar lead is employed.

Aside from the oxygen monitor pulse generator 26, operation of the stimulation device 12 follows conventional principles such as taught, for example, in U.S. Pat. No. 5,342,406 issued to Thompson, U.S. Pat. No. 6,351,672 issued to Park et al., and U.S. Pat. No. 4,712,555 issued to Thomander et al., all of which are incorporated herein by reference in their entireties. Although the present invention is described in conjunction with a cardiac stimulation device being microprocessor based, it is to be understood that it could be implemented in other logic based protocols, such as a state machine mechanization. In such case, the functions undertaken by microprocessor 28 may thus be implemented by the use of the state machine, and in both instances they function as a processor. As is understood, the pulse generator 30, under the control of microprocessor 28, periodically delivers stimulation pulses, via conductors 22 and 24 to selected cardiac sites when it is determined that natural heart contractions have failed to occur. The sense circuit 32 monitors the various cardiac depolarization signals at selected cardiac sites and in the absence of such signals, the microprocessor 28 directs the pulse generator 30 to deliver appropriate stimulation pulses at the selected sites so as to induce proper cardiac muscle contractions. The sense circuit 32 determines the absence of proper depolarization signals by monitoring the voltage at the various stimulation lead electrodes to detect proper voltage patterns.

Figure 2:
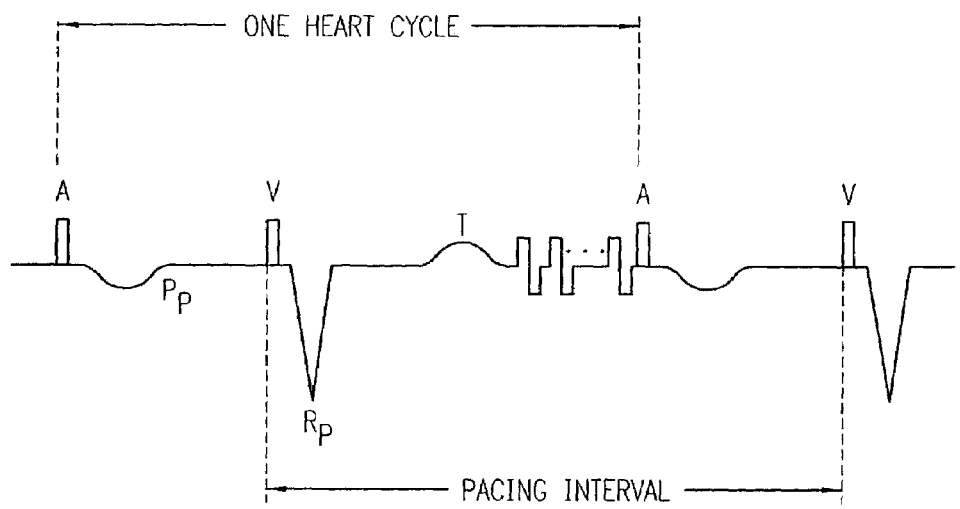
FIG. 2 is a timing diagram showing the relationship between pacing pulses delivered to a heart by a cardiac stimulation device and the heart's response to these pulses.

A representative heart cycle and pacing cycle are shown in FIG. 2, where the stimulation pulse labeled "A" is an atrial stimulation pulse and Pp is the atrial depolarization signal or "P" wave and "V" is a ventricular stimulation pulse and Rp is a ventricular depolarization signal or "QRS" complex. The "T" wave represents the repolarization of the ventricles so that they may be in condition to be stimulated again. For purposes of this application, the polarity of Pp and Rp is inverted to distinguish them between a stimulated response and a naturally occurring response. As will be described later, the region between the "T" wave and the "A" pulse may be utilized by the oxygen monitor pulse generator 26 under the direction of microprocessor 28, for transmitting oxygen monitoring pulses to the oxygen monitoring circuit 25 and for receipt of response data from the oxygen monitoring circuit 25 to microprocessor 28 for blood oxygen content calculations.

Figure 3:
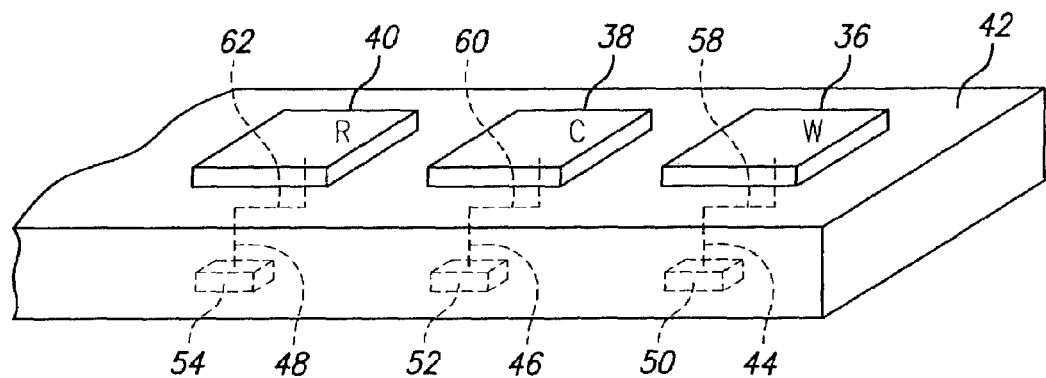
FIG. 3 is a perspective view of the electrodes mounted on a substrate used by the oxygen monitoring circuit of the present invention.

As is shown in FIG. 1, the oxygen monitoring circuit 25 is integrated in stimulation lead 14. The optimum time for placement of the oxygen monitoring circuit 25 in the stimulation lead 14 is during manufacture of the lead. The physical size of the oxygen monitoring circuit 25 is such that no appreciable additional volume is added to the stimulation lead in the region of the sensor placement so as not to interfere with either the stimulation lead's insertion into or retraction from its intended placement in the venous system or with the blood flow in the selected vein. A technique for oxygen sensing in conjunction with a glucose monitoring system, including the system electronics, is described in detail in U.S. Pat. No. 5,497,772, issued to Schulman et al., which is incorporated herein by reference in its entirety. Prior to a discussion of the electronic interface of the oxygen monitoring circuit 25 with the oxygen monitor pulse generator 26 and microprocessor 28, it is informative to understand the physical configuration of the circuit 25. More specifically and with reference to FIG. 3, three metal electrodes, namely a working electrode 36, a counter electrode 38, and a reference electrode 40 are mounted on substrate 42. The substrate is typically a ceramic material known in the art and the electrodes are metalized sections deposited or etched on the substrate using conventional thin film deposition or etching techniques. The working and counter electrodes may be formed of or coated with platinum and the reference electrode may be formed of or coated with silver chloride. Other suitable metals such as gold may also be used. Extending through the substrate 42 are electrically conductive vias 44, 46, and 48 that are electrically coupled to electrodes 36, 38, and 40 respectively. The vias are also electrically coupled to corresponding electrically conductive pads 50, 52, and 54 respectively.

Figure 4A:
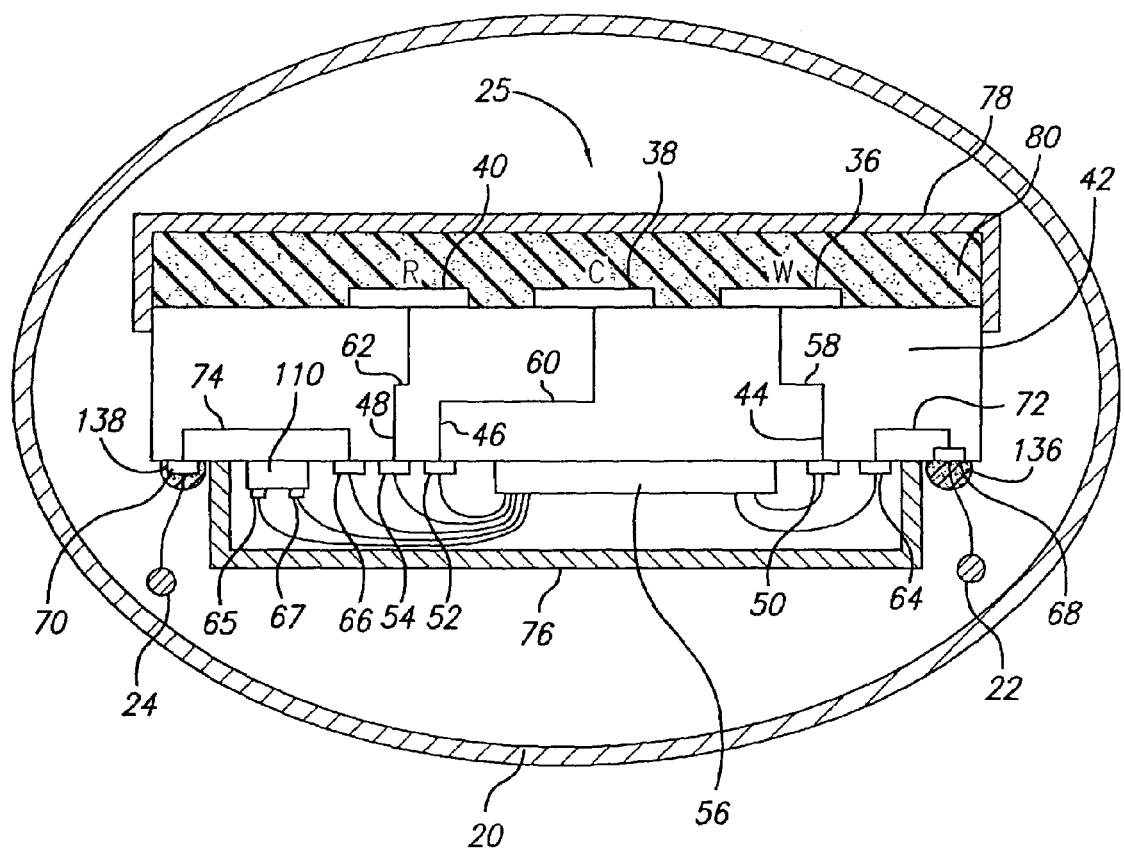
FIG. 4A is a cutaway view of the oxygen monitoring circuit of the present invention, including an IC chip, in an encasing silicone sleeve of a cardiac stimulation lead.

As will be discussed below, the pads 50, 52 and 54 are positioned on the opposite side of the substrate 42 with respect to the placement of the electrodes 36, 38, and 40 respectively, for an electrical interface with a signal processing and data receipt and data transmission-integrated circuits (IC) chip 56 (see FIG. 4A). The vias 44, 46 and 48 have a horizontal portion 58, 60, and 62 respectively, as viewed in FIG. 4A, to ensure against any fluid leakage between the opposite sides of the substrate 42 along the via paths through the substrate and also eliminate any noise contributions resulting from fluid contact with the vias. The IC chip 56 further includes at least two additional internal pads, 64 and 66 that connect to external pads 68 and 70 through vias 72 and 74 respectively. As will be discussed later, the pads 68 and 70 are connected to stimulation lead conductors 22 and 24 respectively and carry electrical signals from the leads to the IC chip 56. Surrounding the IC chip 56 is a sealing cap 76 adapted to provide a hermetic seal completely surrounding the IC chip 56. The horizontal portion of vias 72 and 74 (as depicted in FIG. 4A) provide additional insulation against any potential leakage fluids from penetrating into the IC chip 56.

Another method of providing a hermetic seal is to utilize the IC chip 56 in place of the substrate 42 with the energy storage device included in the IC chip circuit with an overall coating or encapsulation material formed of a thin layer or layers of alumina, zirconia and/or alloys of alumina or zirconia on the IC chip 56 and other components considered as requiring such seal. This construction eliminates the need for the sealing cap 76, wire bonds while the pads 68 and 70 are placed on the opposite side of the IC chip 56, but outside sheath 78. The remainder of the construction remains as shown in FIG. 4B. Encapsulation and hermetic materials and a method of depositing such materials is described in detail in U.S. Pat. No. 6,043,437 issued to Schulman et al. which is incorporated herein in its entirety, by reference.

Completely surrounding the working electrode 36, the counter electrode 38 and the reference electrode 40 is a sheath 78 formed of an oxygen transmissible material, such as silicone rubber having a thickness in the range of about three mils (0.003 inches). The sheath 78, which is also impervious to fluid flow across its surfaces, is sized to provide a pocket within which is disposed an oxygen and electrically conductive thick gel like substance 80, known as "pHema". Completely surrounding the oxygen monitoring circuit 25 is a thicker sheath 20 made typically of silicone rubber, which is known to allow oxygen to pass through its surfaces. The sheath 20 is the outer casing of stimulation lead 14 and the insulated lead conductors 22 and 24 have their metal wires connected to pads 68 and 70 respectively. The uninsulated connection to pads 68 and 70 are coated with an insulation material such as epoxy. Since the signals carried by conductors 22 and 24 are digital or large pacing pulses, the small leakage that may occur will only slightly affect their respective amplitudes, but their timing will remain unaltered. When the oxygen monitoring circuit 25 is placed in a patient's venous system, blood oxygen passes through the sheath 20 and then through sheath 78. The gel 80 contains salt water and is capable of allowing such oxygen to come into contact with each of the electrodes 36, 38, and 40. The principles regarding the measurement of glucose in the patient's blood as taught in the previously identified U.S. Pat. No. 5,497,772, may be extended here for the measurement of blood oxygen. Accordingly, reference is made to FIGS. 5A, 5B and 5C, which represent a schematic of the electrical circuit coupled to the oxygen monitoring circuit 25 for determining the oxygen content in the blood, a graph that qualitatively depicts the relationship between electrical currently delivered and the electrodes of the oxygen monitor circuit 25 and the voltage applied between the electrodes that varies as a function of oxygen content, and a graph that depict the relationship that exists at a fixed electrode voltage between the current flowing through the electrode 38 and the oxygen content, respectively. Referring to FIG. 5A, a trim voltage monitor 86 is coupled between the reference electrode 40 and the working electrode 36 and a current source 84 is coupled between working electrode 36 and counter electrode 38. In the presence of oxygen, current flows through the working electrode 36. The concentration of oxygen in the blood has a direct effect on the level of current flowing through working electrode 36. From FIG. 5B it is observed that the current I and the trim voltage V's, vary as a function of the oxygen concentration. For high concentrations of oxygen $O_2(H)$, a curve 88 establishes a relationship between I and V, and for low concentrations of oxygen $O_2(L)$, a curve 90 establishes a relationship between I and V. Intermediate values of oxygen concentration produce a family of curves between the high and low oxygen concentration values, each curve representing a different oxygen concentration level.

In practice, to measure the blood oxygen concentration, it is required to maintain the trim voltage V at a constant or fixed value, which is typically in the range of about 0.3 to 0.7 volts and preferably at 0.5 volts. This is accomplished by varying the current I until the trim voltage (V) is measured to be 0.5 volts. As will be described below, the feedback control system to maintain the trim voltage at a constant value is undertaken in the IC chip 56. From FIG. 5C is it recognized that the relationship between the current I and the oxygen concentration is substantially linear, so that the oxygen concentration at the working electrode 38 is simply related to the amount of current required to maintain the trim voltage V, at a constant value $V_R$. Accordingly, to determine the oxygen concentration in the blood, it is necessary simply to measure the current I delivered by current source 84.

Figure 6:
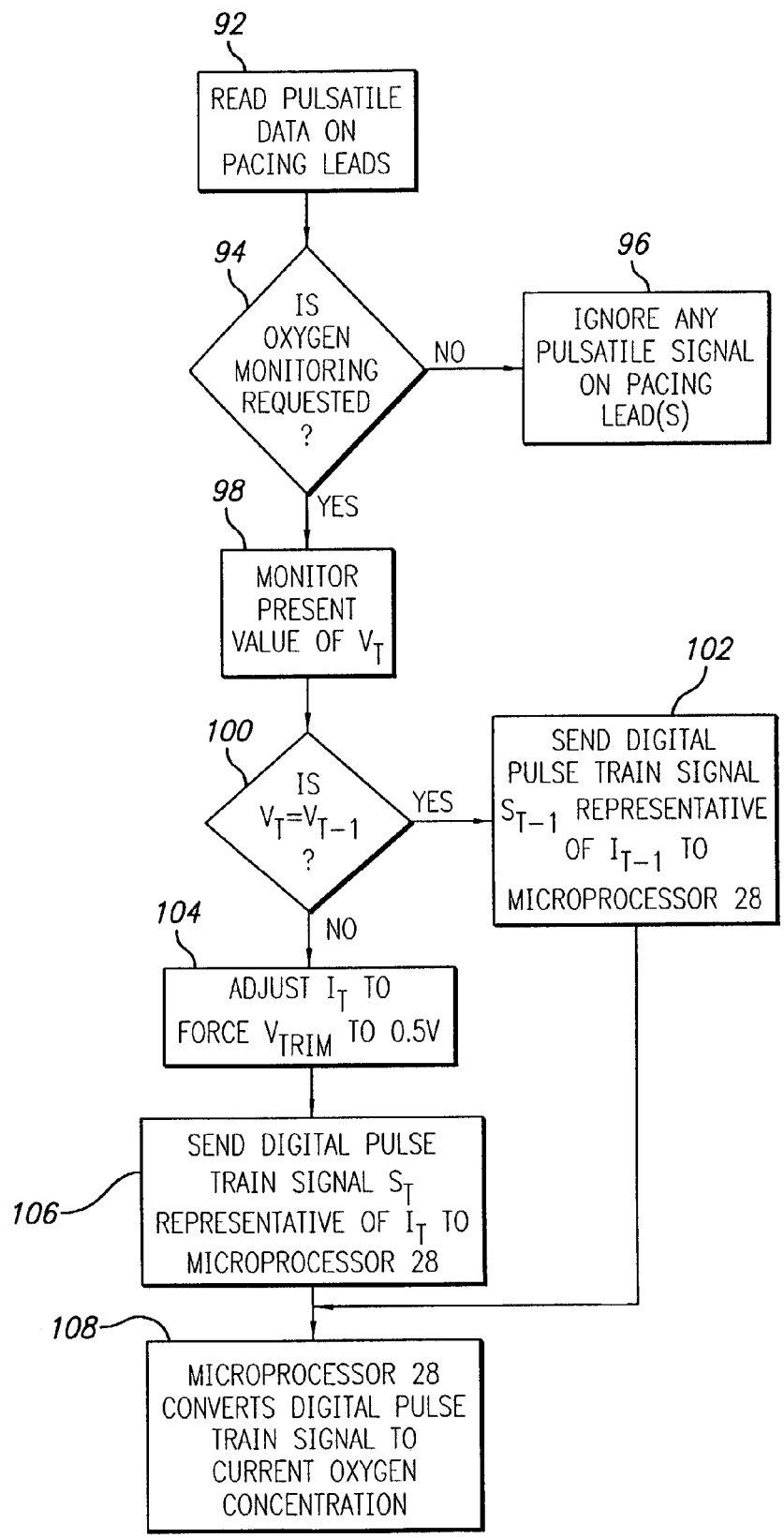
FIG. 6 is a flow chart of the oxygen monitoring method undertaken by the IC chip.

Referring now to FIG. 6, there is shown a flow chart of the signal processing regimen undertaken by the IC chip 56. As shown in FIG. 1, pacing pulses, oxygen monitor pulse generator signals and oxygen concentration signals, are transmitted via stimulation lead conductors 22 and 24. Accordingly at block 92, a pulsatile signal existing on the stimulation lead conductors is monitored. The pulsatile signal is analyzed in block 94 to determine whether it is a cardiac stimulation pulse or a pulse train containing a request to monitor the current value of the blood oxygen concentration. The form of the pulse train signal will be discussed in detail later. If the IC chip 56 determines that no request exists for the determination of the current value of the blood oxygen concentration, then in block 96 the pulsatile signal is ignored and no further action is taken by the IC chip 56. However if a request to monitor the current oxygen concentration exists, the current value of the trim voltage $V_T$ is monitored in block 98 and in block 100, if it determined that the value of $V_T$ is equal to $V_{T-1}$, indicating that the blood oxygen concentration has not changed between successive determinations, the IC chip 56 sends a pulse train $S_{T-1}$ representative of the value of the current $I_{T-1}$ generated by the current source 84 during the prior oxygen concentration determination to the microprocessor 28. However, if $V_T$ does not equal $V_{T-1}$, then in block 104 the IC chip 56 adjusts the value of the current generated by the current source 84 until the present trim voltage $V_T$ equals 0.5 volts. In block 106, a pulse train $S_T$ representative of the present value of the current $I_T$ required to return the trim voltage $V_T$ to 0.5 volts is sent to the microprocessor 28. Although the microprocessor 28 is not contained in IC chip 56, the process undertaken by the microprocessor 28 of converting the pulse train data to the present value of the blood oxygen concentration is depicted in block 108.

An additional advantage of the present invention is that IC chip 56 is coupled to an energy storage device 110, such as rechargeable battery or capacitor (see FIG. 4B) that provides power to the chip so it can undertake the voltage monitoring, current generation, pulsatile signal recognition and generation and other functions necessary to carry out the electrical aspects of the invention. Although the energy storage device has been described as a rechargeable battery, it is to be understood those other energy storage devices, such as a capacitor, are within the contemplation of the present invention. Furthermore, as an alternate embodiment to that shown in FIG. 4B, the energy storage device may be included in the IC chip providing the potential of eliminating the use of a substrate. The pulsatile signals appearing on conductors 22 and 24 are used to recharge the battery 110. To facilitate the recharge function, the battery 110, which is coupled to the IC chip 56 through conductive pads 65 and 67 connected to respective internal pads 64 and 66, may include a half-wave or full-wave rectifier circuit and storage capacitors and in this manner can utilize pulses of both polarities whether they are cardiac stimulation pulses or oxygen interrogation request pulse trains, for the recharge process. The use of the IC chip 56, including programming its functions, especially in view of the specific teachings of this invention, are considered to be within the realm of capabilities of one skilled in the art. Similarly, the use of energy storage devices such as the rechargeable battery, and rectifier circuits are considered within the capabilities of one skilled in the art.

Figure 7:
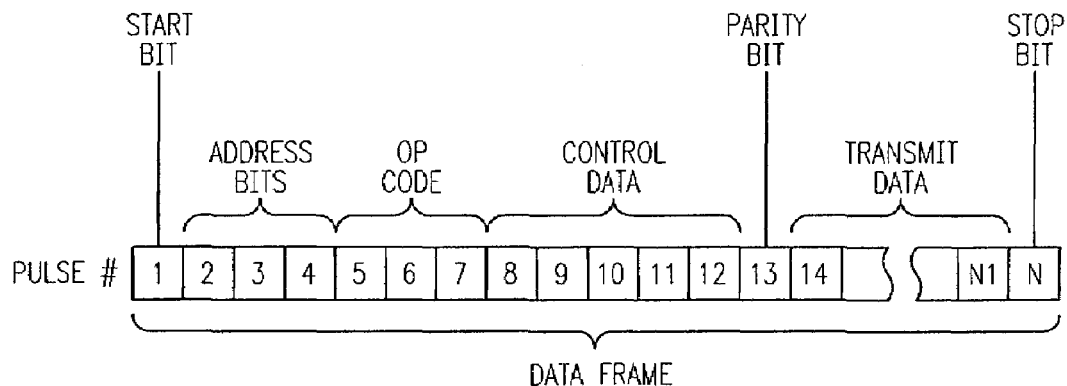
FIG. 7 illustrates a data frame used to communicate between the microprocessor and the oxygen monitoring circuit.
Figure 8:
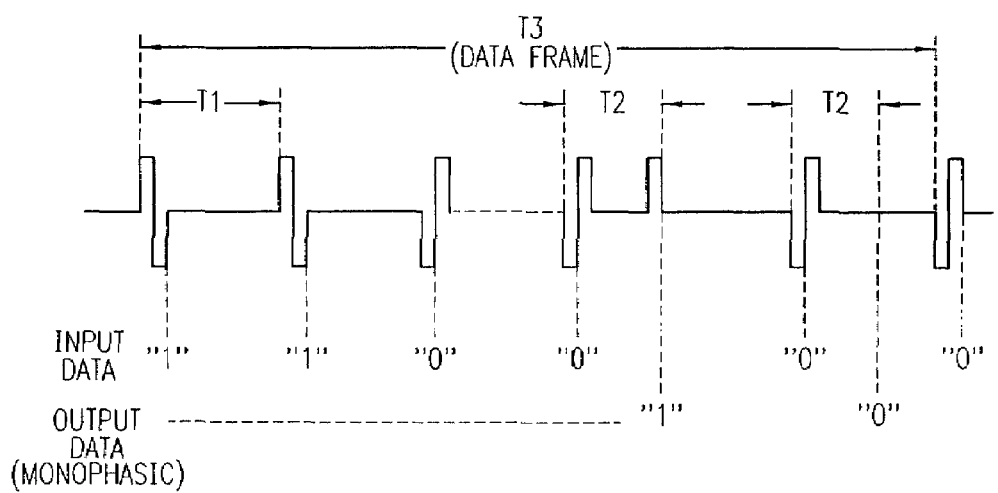
FIG. 8 is a timing diagram that illustrates time multiplexed input and output data within a data frame.

An example of the pulse train used by the oxygen monitor pulse generator 26 is shown in U.S. Pat. No. 5,917,346 issued to Gord, and which is incorporated herein by reference in its entirety. More specifically and with reference to FIGS. 7 and 8, there is shown the oxygen monitor pulse generator 26 data signal sent over conductors 22 and 24 under the control of microprocessor 28. The data frames are of length T3 and within each data frame, N bits of data are found, where N is an integer typically in the range from 8 to 64. A representative assignment of the data bits included in the data frame is shown in FIG. 7. It is noted that the data bits contain a start bit, address bits, OP code bits, control data bits, a parity bit, transmit data bits and a stop bit. The "transmit data bits" portion of the data frame includes parameter information bits relating to the nature, status or value of the respective parameter. As shown in FIG. 7, there are three assigned address bits to provide for eight sensors. However, it is to be understood that additional address bits may be used to provide for a greater number of sensors. The distribution of the bits complies with accepted convention and within the capabilities of one skilled in the art for implementing the signal processing procedures for reading and writing such data frames. The parity bit is used to check for a possible error in the command due to noise. If more than one bit of error might occur, then several bits can be used for checking this possibility. Because the input comprises biphasic data that occurs at a regular interval or rate, e.g., every T1 seconds, the energy contained in such pulse, as described previously, may be utilized to provide the operating power or battery recharge necessary for the operation of the circuits contained within the oxygen monitor circuit 25 and IC chip 56. The typical widths of the pulses are in the range from 0.1 to 1000 microseconds and have a magnitude in the range of from approximately 0.5 to 10 volts. The voltages used depend on the specific IC technology used. For example, 0.5 micron technology requires from about 3 to 5 volts and 0.08 micron technology requires about 0.5 volts.

A binary or logical "1" is represented by a biphasic pulse of one phase, that is, a positive pulse followed by a negative pulse, whereas a binary or logical "0" is represented by a biphasic pulse of the opposite phase that is, commencing with a negative pulse followed by a positive pulse. As an alternate form for the data information returned by the IC chip 56 to the microprocessor 28, a monophasic pulse train may be employed. As is shown in FIG. 2, the interval between the T wave and the atrial stimulation pulse A, is available for use for the transmission and receipt of oxygen related data frames.

One method of generating a monophasic pulse train is to generate a positive pulse to represent a binary or logical "1" and a binary or logical "0" by the absence of a pulse. The pulse train requesting the data can act as the clocking circuit for the oxygen detector and thus determine when a return pulse should be present. Such technique may be used by the present invention and the microprocessor 28 may be programmed to recognize the absence of a pulse as a binary or logical "0". For example and with reference to FIG. 8, the logical "1" appearing at a time T2 after an input data logical "0", is identified as data existing as output data, whereas the logical "0" at a T2 time after the next input data logical "0" is identified as no output data existing In this manner, output data may be identified and transmitted to the microprocessor for processing. It should be noted that pulse widths in the range of from 1 to 10 microseconds, as contemplated by this invention, will have a little or no possibility in stimulating the heart because of the relatively slow cardiac muscle reaction time, thus permitting the use of the conductors 22 and 24 for carriers of both cardiac stimulation and oxygen related pulses. Similarly, circuit design features may be used, if needed, in the IC chip 56, to shield the chip from the effects of relatively long duration high voltage cardiac stimulation pulses.

Figure 9:
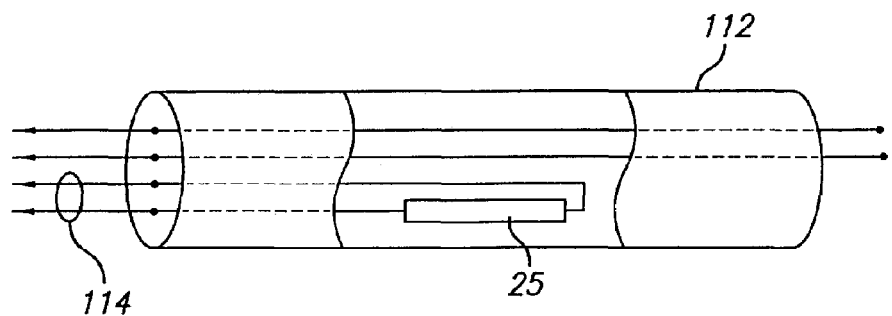
FIG. 9 is an alternate embodiment of the electrical connection of the oxygen monitoring circuit in the cardiac stimulation lead showing a four-wire arrangement.
Figure 10:
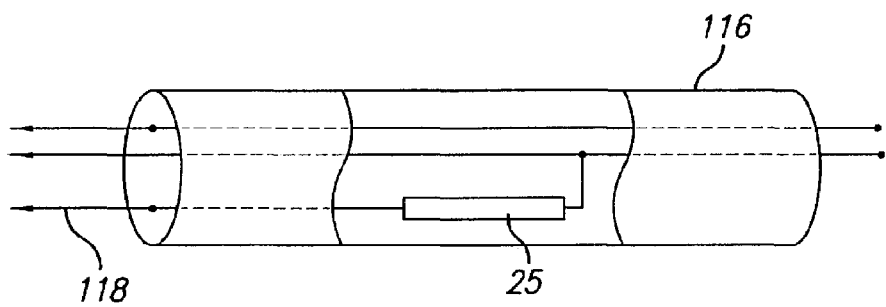
FIG. 10 is an alternate embodiment of the electrical connection of the oxygen monitoring circuit in the cardiac stimulation lead showing a three-wire arrangement.
Figure 11:
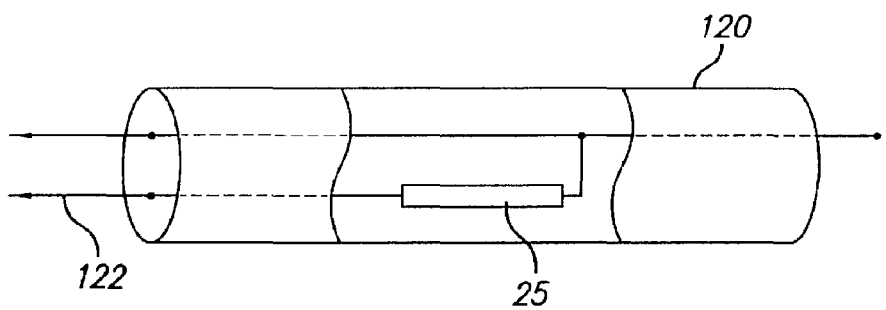
FIG. 11 is an alternate embodiment of the electrical connection of the oxygen monitoring circuit in the cardiac stimulation lead showing a two-wire arrangement.
Figure 12:
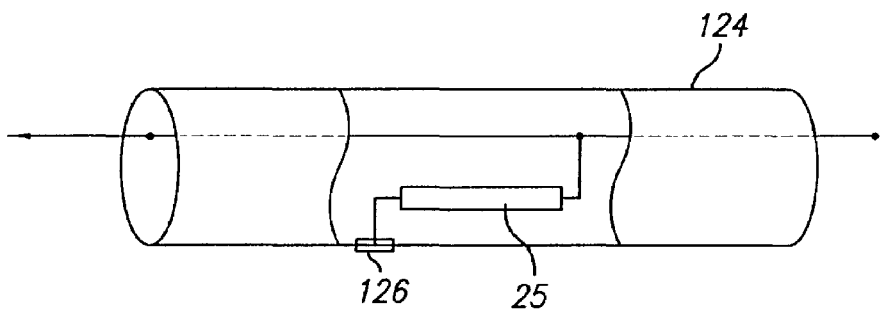
FIG. 12 is an alternate embodiment of the electrical connection of the oxygen monitoring circuit in the cardiac stimulation lead showing a one wire arrangement.

Although the invention has been described with reference to a bipolar lead, it is to be understood that other lead configurations are contemplated by the invention. Accordingly reference is made to FIG. 9 through FIG. 12. showing such other configurations. FIG. 9 shows a bipolar lead 112 having a second pair of conductors 114 devoted exclusively to oxygen monitoring circuit 25. In this manner, the delivery of the oxygen monitoring related pulse trains is independent of cardiac stimulation pulse delivery timing. FIG. 10 shows a bipolar lead 116 having a third conductor 118 functioning as a return for oxygen monitoring circuit 25. FIG. 11 shows a unipolar lead 120 having a second conductor 122 functioning as a return for oxygen monitoring circuit 25. FIG. 12 shows a unipolar lead 124 having a conductive element 126 on the surface of the lead that is connected to oxygen monitoring circuit 25 and that acts as a return through the patient's anatomy in much the same fashion as does the return for a unipolar lead.

Figure 13:
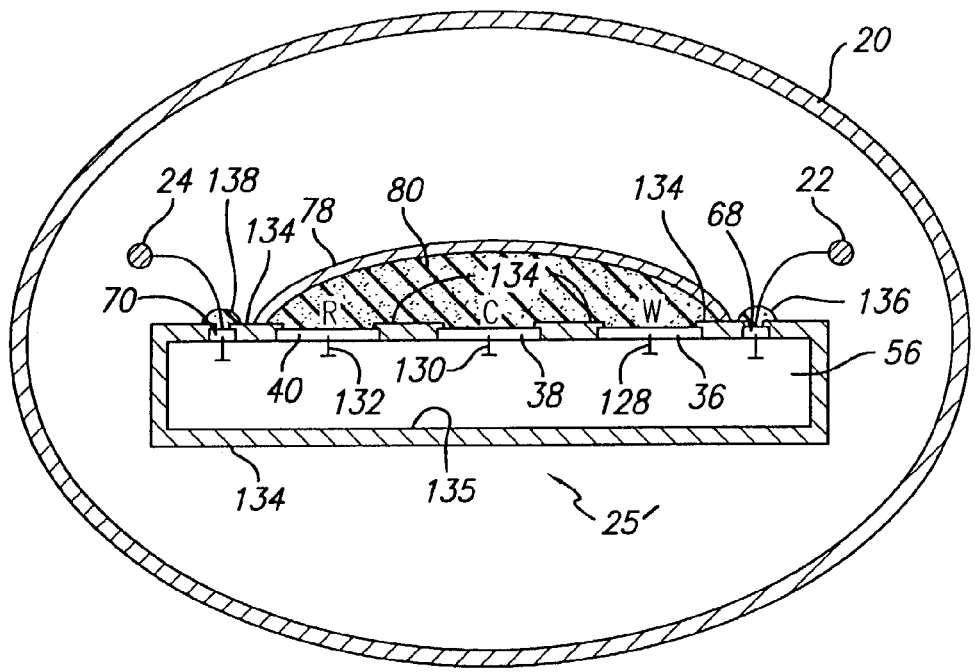
FIG. 13 is a cut away front elevation view of an alternate embodiment of the oxygen monitoring circuit of FIG. 4A showing electrodes mounted directly on the IC chip.

An alternate embodiment of the oxygen monitoring circuit of FIG. 4A is shown in FIG. 13 as monitoring circuit 25'. The monitoring circuit 25' comprises the IC chip 56, with the electrodes 36, 38 and 40 mounted directly on one side of the IC chip. The electrically conductive vias 128, 130 and 132 interconnect the electrodes 36, 38 and 40 respectively, to corresponding terminals on the IC chip 56. The electrodes are immersed in a gel 80 which is encased by a sheath 20, all as previously described. The pads 68 and 70 provide and interface connection between the IC chip 56 and conductors 22 and 24 respectively. With the exception of the sheath 78 and pads 68 and 70, the IC chip 56 is encased by a hermetic sealing cap as previously described or coated by a fluid impervious hermetic material 134. The material 134 also extends around the electrodes 36, 38 and 40 in such a manner so as to insulate the IC chip 56 from the gel 80. An appropriate candidate for such material is aluminum oxide (alumina) as described in U.S. Pat. No. 6,259,937 which is incorporated herein by reference in its entirety. Moreover, a waterproof material 136 and 138 encases the pads 68 and 70 respectively. The waterproof material forms a fluid tight seal around the pads and is preferably, but not restricted to, an epoxy material.

Figure 14:
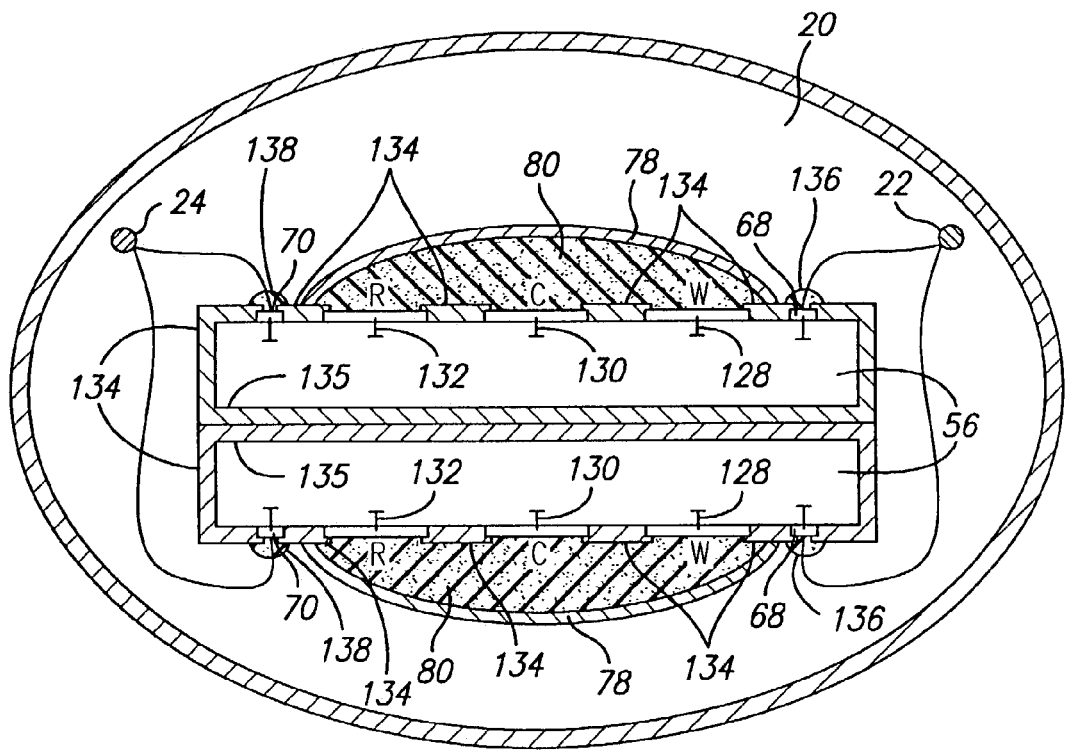
FIG. 14 is a cut away front elevation view of an alternate embodiment of the oxygen monitoring circuit of FIG. 14 showing two IC chip's mounted in back to back relation.

A still further embodiment of the oxygen monitoring circuit of FIG. 4A is shown in FIG. 14 wherein two IC chips (each IC chip being descried above in conjunction with FIG. 13) are arranged such that the underside 135 of each monitoring circuit 25' is in registration and in abutting relationship. As shown in FIG. 14, pads 68 and 70 of each IC chip 56 are electrically connected to conductors 22 and 24 respectively. The connection is insulated with an epoxy 136 and 138 or other waterproof insulating material. Since the timing of the blood oxygen interrogation pulses is the measurement parameter rather than the magnitude of such pulses, a slight amount of leakage in the area of the epoxy insulating material is tolerable. The IC chips are sized small enough such that one or two chips as discussed, fit within a cardiac stimulation lead. An advantage of the embodiment of FIG. 14 is the increased oxygen monitoring capability of two "sensors" over one "sensor".

While the invention herein disclosed has been described by means of specific embodiments and applications thereof, numerous modifications and variations can be made thereto by one skilled in the art without departing from the spirit and scope of the invention as set forth in the claims.

What is claimed is:

1. An implantable cardiac stimulation system comprising:
   a cardiac stimulation lead adapted to be in contact with a patient's blood stream and selected cardiac sites, said stimulation lead having at least one electrical conductor; and
   a stimulation device comprising:
   a processor;
   an oxygen monitoring circuit electrically coupled to said at least one electrical conductor and in contact with the patient's blood stream, said oxygen monitoring circuit configured to monitor the oxygen concentration of the patient's blood;
   a cardiac stimulation pulse generator coupled and responsive to the processor and configured to deliver cardiac stimulation pulses via the cardiac stimulation lead to the selected cardiac sites;
   an oxygen monitoring pulse generator coupled to the processor and configured to generate a biphasic pulse train for application to the at least one electrical conductor between consecutive cardiac stimulation pulses, the pulse train defining a data frame having a pre-determined number of bits including parameter information bits, wherein upon the occurrence of the biphasic pulse train, the oxygen monitoring circuit interrogates the patient's blood during an interval between consecutive cardiac stimulation pulses to measure the blood oxygen concentration utilizing respective ones of the pulse train bits for carrying commands and parameter information between the processor and oxygen monitoring circuit.

2. The system of claim 1 wherein the biphasic pulse train comprises pulses having opposite polarities, representative of a digital "1" and a digital "0", respectively.

3. The system of claim 2 wherein the pulses have pulse widths in the range of about 0.1 to 100 microseconds.

4. The system of claim 1, wherein the oxygen monitoring circuit includes a re-chargeable energy source and wherein said cardiac stimulation pulses are utilized to recharge the energy source.

5. The system of claim 1, wherein the oxygen monitoring circuit includes a re-chargeable energy source and wherein the biphasic pulses are utilized to recharge the energy source.

6. The system of claim 1, wherein the oxygen monitoring circuit includes circuitry to generate a pulse train responsive to the oxygen monitoring pulse train in a format consistent therewith to provide the processor with the results of the interrogation request.

7. The system of claim 6, wherein the pulse train generated by the oxygen monitoring circuit is monophasic.

8. The system of claim 1, wherein the at least one conductor comprises two conductors and the oxygen monitoring circuit is electrically coupled across said two conductors.

9. The system of claim 1, wherein the cardiac stimulation pulse generator is housed in an electrically conductive can in contact with a patient's tissue, and wherein the oxygen monitoring circuit is electrically coupled to the at least one electrical conductor and the patient's tissue.

10. The system of claim 1, wherein the at least one conductor includes a pacing conductor and a return conductor wherein the oxygen monitoring circuit is electrically coupled between the pacing conductor and the return conductor.

11. The system of claim 1, wherein the at least one conductor comprises two pacing conductors and a return conductor wherein the oxygen monitoring circuit is electrically coupled between one of the pacing conductors and the return conductor.

12. The system of claim 1, wherein the at least one conductor comprises a pair of pacing conductors and a second pair of conductors, the oxygen monitoring circuit being electrically coupled across the second pair of conductors, said second pair of conductors in electrical communication with the stimulation device.

13. A cardiac stimulation lead for use with a cardiac stimulation device, the device comprising, a processor, a cardiac stimulation pulse generator coupled and responsive to the processor and configured to deliver cardiac stimulation pulses via the cardiac stimulation lead to selected cardiac sites, an oxygen monitoring pulse generator coupled to the processor and configured to generate a biphasic digital pulse train defining a data frame for application to the cardiac stimulation lead between consecutive cardiac stimulation pulses, the biphasic pulse train having a pre-determined number of bits including parameter information bits, the stimulation lead comprising:
   at least one electrical conductor, said lead adapted to be in contact with a patient's blood stream and selected cardiac sites; and
   an oxygen monitoring circuit electrically coupled to said at least one electrical conductor and adapted to be in contact with the patient's blood stream, said oxygen monitoring circuit configured to monitor the oxygen concentration of the patient's blood, wherein upon the occurrence of the biphasic pulse train, the oxygen monitoring circuit interrogates the patient's blood during an interval between consecutive cardiac stimulation pulses to measure the blood oxygen concentration utilizing respective ones of the pulse train bits for carrying commands and parameter information between the processor and oxygen monitoring circuit.

14. The cardiac stimulation lead of claim 13, wherein the oxygen monitoring circuit includes a re-chargeable energy source and wherein said cardiac stimulation pulses are utilized to recharge the energy source.

15. The cardiac stimulation lead of claim 13, wherein the oxygen monitoring circuit includes a re-chargeable energy source and wherein the biphasic pulses are utilized to recharge the energy source.

16. The cardiac stimulation lead of claim 13, wherein the oxygen monitoring circuit includes circuitry to generate a pulse train responsive to the oxygen monitoring pulse train in a format consistent therewith to provide the processor with the results of the interrogation request.

17. The cardiac stimulation lead of claim 16, wherein the pulse train generated by the oxygen monitoring circuit is monophasic.

18. The cardiac stimulation lead of claim 13, wherein the cardiac stimulation pulse generator is housed in an electrically conductive can in contact with a patient's tissue, and wherein the oxygen monitoring circuit is electrically coupled to the at least one electrical conductor and the patient's tissue.

19. The cardiac stimulation lead of claim 13, wherein the at least one conductor includes a pacing conductor and a return conductor wherein the oxygen monitoring circuit is electrically coupled between the pacing conductor and the return conductor.

20. The cardiac stimulation lead of claim 13, wherein the at least one conductor comprises a pair of pacing conductors and a second pair of conductors, the oxygen monitoring circuit being electrically coupled across the second pair of conductors, said second pair of conductors in electrical communication with the stimulation device.

21. The cardiac stimulation lead of claim 13, wherein the at least one conductor comprises two pacing conductors and a return conductor, wherein the oxygen monitoring circuit is electrically coupled between one of the pacing conductors and the return conductor.

22. The cardiac stimulation lead of claim 13, wherein the at least one conductor comprises two conductors and the oxygen monitoring circuit is electrically coupled across said two conductors.

23. A cardiac stimulation lead for use with a cardiac stimulation device, the device comprising, a processor, a cardiac stimulation pulse generator coupled and responsive to the processor and configured to deliver cardiac stimulation pulses via the cardiac stimulation lead to selected cardiac sites, an oxygen monitoring pulse generator coupled to the processor and configured to generate a biphasic pulse train for application to the cardiac stimulation lead between consecutive cardiac stimulation pulses, the stimulation lead comprising:
   at least one electrical conductor, said lead adapted to be in contact with a patient's blood stream and selected cardiac sites; and
   an oxygen monitoring circuit electrically coupled to said at least one electrical conductor and adapted to be in contact with the patient's blood stream, said oxygen monitoring circuit configured to monitor the oxygen concentration of the patient's blood, wherein the oxygen monitoring circuit interrogates the patient's blood during an interval between consecutive cardiac stimulation pulses to measure the blood oxygen concentration utilizing the biphasic pulse train for carrying commands and parameter information between the processor and oxygen monitoring circuit.

24. A cardiac stimulation lead for use with a cardiac stimulation device, the device comprising, a processor, a cardiac stimulation pulse generator coupled and responsive to the processor and configured to deliver cardiac stimulation pulses via the cardiac stimulation lead to selected cardiac sites, an oxygen monitoring pulse generator coupled to the processor and configured to generate a biphasic pulse train for application to the cardiac stimulation lead, the stimulation lead comprising:
   at least one electrical conductor, said lead adapted to be in contact with a patient's blood stream and selected cardiac sites; and
   an oxygen monitoring circuit electrically coupled to said at least one electrical conductor and adapted to be in contact with the patient's blood stream, said oxygen monitoring circuit configured to monitor the oxygen concentration of the patient's blood, wherein the oxygen monitoring circuit interrogates the patient's blood to measure the blood oxygen concentration utilizing the biphasic pulse train for carrying commands and parameter information between the processor and oxygen monitoring circuit, wherein the oxygen monitoring circuit comprises:
   a working electrode, a counter electrode and a reference electrode;
   an integrated circuit chip electrically coupled to said electrodes and programmed to undertake an oxygen concentration measurement process;
   a current source controlled by said integrated circuit chip and coupled between the working electrode and the counter electrode and configured to supply current between the working and counter electrodes;
   a voltage monitor arranged to detect the voltage across the reference electrode and working electrode; wherein the integrated circuit chip is programmed to control the level of current supplied by the current source and to monitor the detected voltage such that upon exposure of the electrodes to varying levels of oxygen concentration, varying levels of current are caused to flow between the working electrode and counter electrode and wherein the detected voltage is caused to change and further wherein the integrated circuit chip causes the current source to generate a current of a magnitude to return the detected voltage to a preselected reference value, said current magnitude being a direct measure of oxygen concentration, wherein the electrodes are encased in an oxygen conductive gel, comprising pHema.

25. The lead of claim 24 wherein the lead is encased in an oxygen transmissible sheath.

26. The lead of claim 24 wherein the lead is encased in a silicone sheath extending the length thereof.

27. The lead of claim 24 wherein said working electrode, counter electrode and reference electrode are mounted on one face of a ceramic substrate and the integrated circuit chip is mounted on an opposing face of the substrate and wherein there are electrical conductors passing through the substrate interconnecting the electrodes with corresponding terminals of the integrated circuit chip, the conductors having a first portion extending through the substrate in a first direction and a second portion traversing through the substrate at a second direction being substantially orthogonal to the first direction.

28. A sensor for use in a cardiac stimulation lead to measure oxygen concentration in a patient's blood comprising:
   a substrate having opposite facing first and second sides, a plurality of electrodes mounted on the first side of the substrate, the electrodes immersed in an oxygen and electrically conductive gel, the gel being encased in a fluid impervious and oxygen transmissible sheath;
   an IC chip mounted on the second side of the substrate, the IC chip being encased within a sealing cap hermetically sealed to the second side of the substrate;
   a plurality of pads located on the substrate outside of the sealing cap and wherein a plurality of hermetic vias selectively coupled to the IC chip and pads provides electrical communication therebetween;
   and
   a plurality of electrical conductors passing through the substrate and interconnecting the electrodes to the IC chip, wherein said sensor is sized to fit within a cardiac stimulation lead.

29. The sensor of claim 28 wherein the substrate comprises a ceramic hermetic material.

30. The sensor of claim 28 further comprising an energy storage device adapted to provide energy to the IC chip.

31. The sensor of claim 30 wherein the energy storage device is a capacitor.

32. The sensor of claim 30 wherein the energy storage device comprises a rechargeable battery.

33. The sensor of claim 30 wherein the energy storage device forms a part of the IC chip.

34. An implantable cardiac stimulation system comprising:
- a cardiac stimulation lead adapted to be in contact with a patient's blood stream and selected cardiac sites, said stimulation lead having at least one electrical conductor; and
- a stimulation device comprising:
- a processor; and a cardiac stimulation pulse generator coupled and responsive to the processor and configured to deliver cardiac stimulation pulses via the cardiac stimulation lead to the selected cardiac sites, said cardiac stimulation lead further comprising an oxygen monitoring circuit electrically coupled to said at least one electrical conductor and in contact with the patient's blood stream, said oxygen monitoring circuit configured to monitor the oxygen concentration of the patient's blood and transmit a digital signal related to said oxygen concentration to the stimulation device, wherein the stimulation device further comprises an oxygen monitoring pulse generator coupled to the processor and configured to generate a biphasic pulse train for application to the at least one electrical conductor between consecutive cardiac stimulation pulses, the pulse train defining a data frame having a predetermined number of bits including parameter information bits, said oxygen monitoring circuit configured to detect the existence of the biphasic pulse train, wherein upon the detection of the biphasic pulse train, the oxygen monitoring circuit interrogates the patient's blood during an interval between consecutive cardiac stimulation pulses to measure the blood oxygen concentration utilizing respective ones of the pulse train bits for carrying commands and parameter information between the processor and oxygen monitoring circuit.

* * * * *